US005937790A

United States Patent [19]
Ito et al.

[11] Patent Number: 5,937,790
[45] Date of Patent: Aug. 17, 1999

[54] ANTI-STRESS AGENT FOR ANIMALS AND A METHOD OF REDUCING STRESS IN ANIMALS

[75] Inventors: Shinobu Ito; Eiji Ogata, both of Tokyo; Masahiro Yamada, Ibaraki, all of Japan

[73] Assignee: Showa Denko Kabushiki Kaisha, Tokyo, Japan

[21] Appl. No.: 08/993,714

[22] Filed: Dec. 18, 1997

Related U.S. Application Data

[60] Provisional application No. 60/047,099, May 19, 1997.

[30] Foreign Application Priority Data

Dec. 18, 1996 [JP] Japan .................................. 8-354314

[51] Int. Cl.$^6$ .......................... A01K 29/00; A23K 1/165; A23K 1/17

[52] U.S. Cl. .......................... 119/174; 119/200; 424/439; 424/442

[58] Field of Search ..................... 119/200, 215, 119/230, 51.01, 174, 204; 426/2; 424/439, 442

[56] References Cited

U.S. PATENT DOCUMENTS

| | | | |
|---|---|---|---|
| 4,161,158 | 7/1979 | Kartesz | 119/230 X |
| 4,647,672 | 3/1987 | Seib et al. | 549/222 |
| 5,030,657 | 7/1991 | Burtle et al. | 426/805 X |
| 5,215,767 | 6/1993 | Mitsuhashi | 426/2 X |
| 5,571,527 | 11/1996 | Nishimura et al. | 424/438 |
| 5,657,718 | 8/1997 | Drozdowski | 119/230 |
| 5,725,893 | 3/1998 | Pittet et al. | 119/204 X |

OTHER PUBLICATIONS

Bioavailability of L–Ascorbyl–2–Polyphosphate in Guinea Pigs, *Bioavailability*, 1993, pp. 325–330.
Chemical Abstracts; vol. 126, No. 11, Mar. 17, 1997, no. 126:224586d; Effect of heat stress and L–ascorbic acid–2–phosphate magnesium on plasma and liver thiobarbituric . . . concentrations.
Patent Abstract of Japan, JPA 06220081.
Effect of Magnesium–L–ascorbyl–2–phosphate on Cutaneous Damage Induced by UVB Irradiation; *Photomedicine and Photobiology*, vol. 17, 1995, pp. 39–40.
A comparison of the effect of silicone coated ascorbic acid and ascorbyl phosphate on the course of ichthyophthirisis in rainbow trout, *Oncorhynchus mykiss, Journal of Fish Diseases*, 1995, vol 18, pp. 347–355.
Effects of Ascorbyl–2–Polyphosphate on Adrenocortical Activation and Fear–Related Behavior in Broiler Chickens; *Poultry Science*, 1994, vol. 73(1); pp. 194–201.

*Primary Examiner*—Jack W. Lavinder
*Assistant Examiner*—Yvonne R. Abbott
*Attorney, Agent, or Firm*—Sughrue, Mion, Zinn, Macpeak & Seas, PLLC

[57] ABSTRACT

An anti-stress agent for animals for reducing the growth inhibition or mortality of animals and a method of reducing stress using a feed composition having blended therein the anti-stress agent. The anti-stress agent for animals comprises one or more substances selected from L-ascorbic acid-2-phosphoric acid, a salt thereof and an L-ascorbic acid-2-glucoside, as an active ingredient, for inhibiting the increase of blood plasma lactate dehydrogenase (LDH), malate dehydrogenase (MDH) and aspartate aminotransferase (AspAT) and for inhibiting the increase of stress proteins in blood, which occur when animals are placed under stress. Also disclosed is a feed composition comprising the anti-stress agent, and a method of reducing the stress of animals by supplying the same as feed.

16 Claims, No Drawings

ANTI-STRESS AGENT FOR ANIMALS AND A METHOD OF REDUCING STRESS IN ANIMALS

CROSS REFERENCE TO RELATED APPLICATIONS

This application is an application filed under 35 U.S.C. §111(a) claiming benefit pursuant to 35 U.S.C. §119(e)(i) of the filing date of the Provisional Application 60/047,099, filed May 19, 1997, pursuant to 35 U.S.C. §111(b).

FIELD OF THE INVENTION

The present invention relates to an anti-stress agent for animals and a method of reducing stress in animals. More specifically, the present invention relates to an anti-stress agent for reducing the stress of animals by inhibiting the increase of LDH, MDH and AspAT as plasma enzymes in blood and the increase of stress proteins which occur when animals are in stress. The present invention also relates to a method of reducing stress by administering the anti-stress agent to animals.

The anti-stress agent for animals of the present invention can prevent the stress reaction of animals and inhibit various disorders accompanying the stress, such as a loss in body weight and a reduction in immunity.

BACKGROUND OF THE INVENTION

Nutritionally, L-ascorbic acid is a very important nutrient, and this single substance or a salt or a derivative thereof is added to a large number of animal feedstuffs.

Particularly in recent years, livestock such as cattle and pigs, and useful marine animals such as rainbow trout, sweet fish, carp, sea bream, salmon, eel, yellow tail, globefish, flatfish, tuna, horse mackerel and prawn are bred or raised at high density. Also, dogs and cats are prevented from running off and are left in noisy places. Accordingly, these animals are inevitably subject to stress. Under such a breeding environment, these animals suffer from stress even in a normal temperature state.

Therefore, the requirement for ascorbic acid is considered to be high as compared with the case of normal breeding conditions. Furthermore, the lack in intake of ascorbic acid causes phenomena such as a loss in body weight, a reduction in immunity and an increase in morality, and incurs enormous economic damage to breeders. Particularly, under a high temperature environment in summer or under a low temperature environment in winter, the stress is intensified and the economic damage increases.

In order to reduce the stress, ascorbic acid has been added to feed for various kinds of animals. However, the L-ascorbic acid in general is prone to oxidation decomposition, and is swiftly deactivated even if it is added to feed. Accordingly, because of this problem, the effect is difficult to maintain. Particularly, in recent years, the heating-type granulating machine commonly used in feed production, such as a pellet mill and an extruder, uses a high temperature as the raw material temperature. Accordingly, other problems are also caused such that L-ascorbic acid in general is rapidly decomposed. Furthermore, because of its poor absorptivity, satisfactory effects cannot be provided even if it is added to feed or the like.

A general technique for solving these problems is to coat a fine grain of inexpensive ascorbic acids and blend the grains with feed. This technique is proposed, for example, in JP-A- 52-15812 (the term "JP-A" as used herein means an "unexamined published Japanese patent application"), JP-A-53-127819, JP-A-54-109962, JP-A-54-154514, JP-A-55-4913, JP-A-57-59803, JP-A-57-85317, JP-A-58-205461, JP-A-59-44327, JP-A-63-164864, JP-A-63-258813, JP-A-64-3118, JP-A-64-3119, JP-A-1-500113, JP-A-1-296953 and JP-A-2-46259.

The coating techniques disclosed in these patent publications are common in that the coated ascorbic acid particles are finely granulated to a particle size of 1 mm or less. This prevents the coated particles from fracturing during the crushing step in the production process of feed or the like. As a result, the surface area is large and oxygen in the air readily permeates therein. This gives rise to a problem in that the coated L-ascorbic acid is easily oxidation decomposed in the production and distribution process of feed in a high-temperature pressure molding machine for processing feed.

Accordingly, a method of adding a stabilized L-ascorbic acid derivative to feed that resists oxidation, such as L-ascorbic acid-2-sulfate, has been proposed. For example, JP-A-49-24783 discloses a method of adding ascorbic acid-2-benzoate, ascorbic acid-2,6-dipalmitate, ascorbic acid-3-palmitate, ascorbic acid-3-stearate, ascorbic acid-3,6-distearate or ascorbic acid-2-phosphate, to artificial feed for silkworms.

Among these, ascorbic acid-3-palmitate, ascorbic acid-3-stearate, ascorbic acid-3,6-distearate and ascorbic acid-2-phosphate are substances which are incapable of exhibiting satisfactory stability against heat or oxidation. However, in the production conditions of silkworm feed, the nutrient components including an ascorbic acid are generally processed at a mild temperature of 65° C. or lower. Therefore, stability is not a problem in the case of silkworm feed. However, recent production processes of feed in a high-temperature molding machine include processing at 70° C. or higher for imparting water resistance, and almost all of the above-described ascorbic acids are disadvantageously decomposed due to the high temperature.

Furthermore, although L-ascorbic acid-2-sulfate, L-ascorbic acid-2-benzoate and ascorbic acid-2,6-dipalmitate are stable against heat or oxidation, they yet have a problem in that conversion by an intracorporeal enzyme into ascorbic acid occurs with difficulty in some animals and the ascorbic acid activity cannot be satisfactorily exerted.

On the other hand, the stress reaction of animals is closely related to the degree of change in various environments where the animals are living, more specifically, a change in environmental factors such as temperature, light, nutrients or breeding density. When the environmental change is small, animals adjust their metabolism without causing a large change in the internal metabolic control mechanism. However, when the environmental change is large, animals can difficultly adapt their metabolism to the change within a short period, and try to put into effect a qualitatively different metabolic control for sustaining and continuing life.

In general, it is known that as the environmental change is larger, the stress reaction that is generated in the animal body intensifies (as described by Yousef, M. K., *Stress Physiology in Livestock*, Vol. I & II, CRC Press (1985); Young B. A. et al., *J. Animal Science*, 67, 2426–2432 (1989); Yamada, M. and Tanaka, M., *Proc. XIX World's Poultry Congress*, 1992, pp. 43–47; Siegel, H. S., *Br. Poult. Sci.*, 36, 3–22 (1995); and Yamada et al., *Proc. 10th European Poultry Nutrition Symposium*, 1995, pp. 373–374).

One example of the effect of ambient temperature on the physiological and production functions of homeotherms such as livestock and poultry is reported by Yamada, *Dobutsu Seisan to Kankyo Chosetsu, Shinpan, Seibutsu Kankyo Chosetsu Handbook* (*Animal Production and Environmental Control, New Version, Biological Environment Control Handbook*), pp. 234–248 (1995). More specifically, in the temperature region of from 18 to 26° C., domestic fowl actively exercises its laying function and does not suffer from any outstanding stress reaction. However, if the ambient temperature enters the region of from 26 to 32° C., the breathing function or behavior form starts changing and signs of stress reaction are observed. If the ambient temperature reaches the region of from 32 to 36° C., the degree of temperature stress becomes large. Accompanying it, the breathing turns into panting breath, the hydroposia or diet behavior becomes very unusual and the laying function is extremely reduced to thereby cause serious economic damage in poultry farming. If the ambient temperature reaches 36° C. or higher, not only the breathing form but also important physiological functions such as the thermoregulation function indispensable to sustain life start to become affected, and the nature of various functions are altered to cope with the life crisis.

In the above-described state, the sustainment of life is a most important issue and therefore, domestic fowl suppress the normal biological substance synthesizing function and accelerate the synthesis of stress proteins to undergo biophylaxis to the extent possible. In this way, the stress reaction in the living body changes to accompany the change in ambient temperature. Also, the physiological constituent factors of the stress reaction include a change in the concentration of biological components related to important metabolic functions and the change in the activity of enzymes contiguous to the substance conversion. In particular, the appearance of enzymatic activity closely related to the biological energy metabolism or appearance of stress proteins for the purpose of biophylaxis serves as a physiological index for assessing the degree of the stress reaction.

The change in metabolic function involves a large number of metabolic pathways such as the saccharometabolism, lipid metabolism and amino acid metabolism in the liver or kidney, and the dismutation metabolism between carbohydrates and amino acids. LDH and MDH are related to the saccharometabolism, and AspAT is related to the carbohydrate and amino acid metabolism. Thus, these are important enzymes. It has recently been reported that an increase in the concentration of LDH, MDH or AspAT activity in blood indicates a biological stress reaction from the aspect of metabolic function. Furthermore, suppression of the stress reaction is a very important matter in breeding livestock with high added value.

The stress protein has several molecular species and the molecular species which is produced depends on the property of the stress reaction. Appearance of the stress protein 80–85 KDa in the plasma of egg layers has been confirmed, but this does not apply to other animals (see, Lindquist, S., *Annu. Rev. Biochem.*, (1986); Morimoto, R. I. and Milarski, K. L., *Stress Proteins in Biology and Medicine*, pp.323–359 (1990); Siegel, H. S., *Br. Poult. Sci.*, 36, 3–22 (1995)).

Reducing or preventing the production of stress proteins in the biophylaxis reaction is a very important issue for healthy and effective breeding of animals. Thus, there has been a demand for the development of a method for controlling and reducing the stress reaction.

When an animal is placed under stress, the stress reaction such as an increase or fluctuation in LDH, MDH or AspAT in blood is observed. However, in many cases, the stress phenomenon capable of externally visual observation, such as a loss in body weight or a reduction in eggshell strength, is not generated and even when it appears, the phenomenon is very often recognized after the lapse of a fairly long time. However, when the stress reaction continues for a long period or when other stress reactions such as infectious diseases multiply, the stress of animals is gradually accumulated and amplified. This may cause serious disease or result in the deterioration of meat quality, egg quality or milk quality before the livestock manager becomes aware of the problem. In conventional techniques, a method capable of satisfactorily suppressing the stress reaction such as an increase or fluctuation of LDH, MDH or AspAT in blood has not been reported.

Thus, in recent highly and intensively efficient stockbreeding or poultry farming, awareness of the stress reaction that is not visually observable and a means for suppressing the same has been an important issue in view of the breeding control of healthy livestock. Furthermore, it has been found that the stress reaction is reliably detected by determining the LDH, MDH or AspAT in the blood of animals.

As described above, the increase of plasma LDH, MDH or AspAT and the increase of stress proteins in blood, as a stress reaction of animals, is a very important physiological index for stress. However, the proposals hitherto reported with respect to stress suppression include neither an anti-stress agent for animals capable of detecting and suppressing the stress reaction of useful livestock nor a method of reducing the stress of animals by administering such an anti-stress agent.

Furthermore, although a method of orally administering vitamin C to egg layers raised in a high temperature environment to increase eggshell strength has been reported, an overall method of preventing the stress imposed on a living animal by suppressing the increase of plasma LDH, MDH and AspAT and the increase of stress proteins in blood, as important physiological indices for stress, has not yet been found.

SUMMARY OF THE INVENTION

It is therefore an object of the present invention to develop an anti-stress agent for animals, for suppressing the increase of plasma LDH, MDH or AspAT and stress proteins in blood, which can be detected as a stress reaction of animals, and for reducing the growth inhibition or mortality of animals. It is also an object of the present invention to develop a method of reducing stress in animals using the anti-stress agent.

The present inventors have made extensive investigations to identify substances free of decomposition even in the production process of feed using a high-temperature heat molding machine, which substances are capable of exhibiting a satisfactorily high anti-stress activity of ascorbic acid to a wide range of useful economic animals, such as cattle, pigs, dogs, cats, rainbow trout, sweet fish, carp, sea bream, salmon, eel, yellow tail, globefish, flatfish, tuna or horse mackerel, which are absorbed at a high ratio and which have an effect on the above-described stress reaction. As a result, the present inventors discovered that when L-ascorbic acid-2-monophosphate, an L-ascorbic acid-2-glucoside or a salt thereof is used as an L-ascorbic acid derivative, the increase of stress plasma LDH, MDH and AspAT and stress proteins in blood can be advantageously suppressed. The present inventors further succeeded in finding a formulation which can reinforce the stress suppression (reduction) of these substances. More specifically, the objects of the present invention have been attained by providing:

(1) a method for inhibiting in animals an increase of blood plasma lactate dehydrogenase (LDH), malate dehydrogenase (MDH) and aspartate aminotransferase (AspAT) and for inhibiting an increase of stress proteins in blood, occurring when said animals are subjected to stress, which comprises administering to animals an anti-stress agent comprising one or more substances selected from the group consisting of L-ascorbic acid-2-phosphoric acid, a salt thereof and an L-ascorbic acid-2-glucoside, as an active ingredient;

(2) the method as described in item (1), wherein said anti-stress agent further comprises an antioxidant substance blended with the one or more substances selected from the group consisting of L-ascorbic acid-2-phosphoric acid, a salt thereof and an L-ascorbic acid-2-glucoside;

(3) the method as described in item (2), wherein the antioxidant substance is selected from the group consisting of carotene, astaxanthin, lutein, dl-α-tocopheryl acetate, α-tocopherol, SOD, glutathione and catechins;

(4) a method for inhibiting in animals an increase of blood plasma lactate dehydrogenase (LDH), malate dehydrogenase (MDH) and aspartate aminotransferase (AspAT) and for inhibiting an increase of stress proteins in blood, occurring when said animals are subjected to stress, which comprises administering to animals, as a premix, an animal drug or a nutrient reinforcement, a feed composition having blended therewith an anti-stress agent as described in any one of items (1) to (3);

(5) a method of reducing stress in animals, which comprises administering 0.03 g/kg-body weight or more of one or more substances selected from the group consisting of L-ascorbic acid-2-phosphoric acid, a salt thereof and an L-ascorbic acid-2-glucoside, for inhibiting an increase of blood plasma lactate dehydrogenase (LDH), malate dehydrogenase (MDH) and aspartate aminotransferase (AspAT) and for inhibiting an increase of stress proteins in blood, which occur when said animals are subjected to stress;

(6) a method of reducing stress in animals, which comprises simultaneously administering 0.03 g/kg-body weight or more of one or more substances selected from the group consisting of L-ascorbic acid-2-phosphoric acid, a salt thereof and an L-ascorbic acid-2-glucoside, as an active ingredient, and 0.02 g/kg-body weight or more of another antioxidant substance, for inhibiting an increase of blood plasma lactate dehydrogenase (LDH), malate dehydrogenase (MDH) and aspartate aminotransferase (AspAT) and for inhibiting an increase of stress proteins in blood, which occur when said animals are subjected to stress;

(7) a method of reducing stress in animals as described in item (5) or (6), wherein the animal is selected from the group consisting of cattle, pigs, dogs, cats, rainbow trout, sweet fish, carp, sea bream, salmon, eel, yellow tail, globefish, flatfish, tuna, horse mackerel and prawn;

(8) a feed composition prepared by blending with animal feed an anti-stress agent for animals containing one or more substances selected from the group consisting of L-ascorbic acid-2-phosphoric acid, a salt thereof and an L-ascorbic acid-2-glucoside, as an active ingredient, in a blending ratio of 300 ppm or more in terms of the active ingredient;

(9) a feed composition prepared by blending with animal feed an anti-stress agent for animals containing 300 ppm or more of one or more substances selected from the group consisting of L-ascorbic acid-2-phosphoric acid, a salt thereof and an L-ascorbic acid-2-glucoside, as an active ingredient, and 200 ppm or more of an antioxidant substance;

(10) a method of reducing stress in animals, which comprises supplying a feed composition described in item (8) or (9) which is prepared by blending with animal feed an anti-stress agent for animals containing 300 ppm or more of one or more substances selected from the group consisting of L-ascorbic acid-2-phosphoric acid, a salt thereof and an L-ascorbic acid-2-glucoside, as an active ingredient, and 200 ppm or more of an antioxidant substance, to cattle, pigs, dogs, cats, rainbow trout, sweet fish, carp, sea bream, salmon, eel, yellow tail, globefish, flatfish, tuna, horse mackerel or prawn; and

(11) a feed composition as described in item (8) or (9), wherein the feed composition prepared by blending with animal feed an anti-stress agent for animals containing 300 ppm or more of one or more substances selected from the group consisting of L-ascorbic acid-2-phosphoric acid, a salt thereof and an L-ascorbic acid-2-glucoside, as an active ingredient, and 200 ppm or more of an antioxidant substance, is a feed composition heated at 80° C. or higher in an extruder, expander, pellet machine or dryer.

DESCRIPTION OF THE PREFERRED EMBODIMENTS

The present invention is described in more detail below.

The term "a salt" in the expression "L-ascorbic acid-2-phosphoric acid, an L-ascorbic acid-2-glucoside or a salt thereof" as an active ingredient of the present invention means a salt of a metal selected from metals such as an alkali metal and an alkaline earth metal (preferably a sodium salt or a magnesium salt).

Examples of the salt of L-ascorbic acid-2-phosphoric acid for use in the present invention include magnesium L-ascorbic acid-2-monophosphate, sodium L-ascorbic acid-2-monophosphate, potassium L-ascorbic acid-2-monophosphate, calcium L-ascorbic acid-2-monophosphate and aluminum L-ascorbic acid-2-monophosphate. Examples of the salt of L-ascorbic acid-2-glucoside include 2-O-α-D-glucopyranosyl-L-ascorbate (as disclosed in JP-A-5-117290), and preferred examples thereof include magnesium L-ascorbic acid-2-monophosphate, L-ascorbic acid-2-phosphate and 2-O-α-D-glucopyranosyl-L-ascorbate.

When an antioxidant is blended with the anti-stress agent comprising L-ascorbic acid-2-phosphoric acid, a salt thereof or an L-ascorbic acid-2-glucoside, as an active ingredient of the present invention, higher effects can be attained for suppressing the increase in plasma LDH, MDH and AspAT and stress proteins in blood which accompanies the stress reaction.

Examples of the antioxidant which can elevate the effect of the present invention include dl-α-tocopherol, dl-α-tocopheryl acetate, vitamin E and a derivative thereof; antioxidants such as erythorbic acid, tea extract, polyphenols and ethoxychin; carotenoids such as astaxanthin; organic acids such as citric acid and glycine; phosphoric acids such as phosphoric acid and metaphosphoric acid; and stabilized L-ascorbic acids such as L-ascorbic sulfate and L-ascorbic palmitate (excluding L-ascorbic acid-2-phosphoric acid, a salt thereof and an L-ascorbic acid-2-glucoside). In particular, when the anti-stress agent of the present invention is used in combination with one or more antioxidant substances selected from carotene, astaxanthin, lutein, dl-α-tocopheryl acetate, α-tocopherol, SOD, glutathione and catechins, the action of suppressing the increase of animal stress plasma LDH, MDH and AspAT and stress proteins in blood is intensified.

The anti-stress agent for animals blended with a feed composition of the present invention may have any drug shape formed for the purpose of administering nutrients or useful drugs into the body of useful animals or reinforcing them. Representative examples thereof include feedstuffs, premix agents, vitamin agents and animal medicines.

One or more substances selected from an L-ascorbic acid-2-monophosphoric acid, a salt thereof and an L-ascorbic acid-2-glucoside, as an active ingredient of the present invention, is administered to animals at a dosage of 0.03 g or more, preferably from 0.03 to 1.5 g, more preferably from 0.03 to 0.6 g, per 1 kg of the animal body weight, irrespective of the kind of animal.

When one or more substances selected from an L-ascorbic acid-2-monophosphoric acid, a salt thereof and an L-ascorbic acid-2-glucoside is added to a normal feed and then administered, the substance is blended in an amount of 300 ppm or more based on the entire weight of the feed.

When the anti-stress agent for animals is used in combination with an antioxidant substance, one or more substances selected from L-ascorbic acid-2-monophosphoric acid, a salt thereof and an L-ascorbic acid-2-glucoside, as an active ingredient of the present invention, is administered at a dosage of 0.03 g or more per 1 kg of the animal body weight, irrespective of the kind of animal, and together therewith, one or more antioxidant substances is administered at a dosage of from 0.02 g or more, preferably from 0.02 to 1 g, more preferably from 0.02 to 0.1 g, per 1 kg of the animal body weight, irrespective of the kind of animal.

Furthermore, when the anti-stress agent for animals is used in combination with an antioxidant substance and added to a feedstuff, irrespective of the kind of animal, 300 ppm or more of one or more substances selected from an L-ascorbic acid-2-monophosphoric acid, a salt thereof and an L-ascorbic acid-2-glucoside, as an active ingredient of the present invention, and 200 ppm or more of one or more antioxidant substances are simultaneously blended to the feed for administration.

Conventionally, an ascorbic acid has been added to feed for animals so as to reduce the stress of useful animals. However, this addition exhibited the following problems. Namely, L-ascorbic acid in general has poor heat resistance and is prone to oxidation decomposition and accordingly, it is difficult to store and handle; in the case of adding to feed or the like, high-temperature heating cannot be used which is performed in the process of forming or drying the feed after blending for sterilizing or disinfecting or to accelerate conversion of the feed into gluten and thereby improve digestibility of the protein; if this high-temperature heating operation is carried out, the added L-ascorbic acid is quickly deactivated and its effect is hardly maintained; and since a heating-type granulating machine commonly used in feed production in recent years, such as a pellet mill and an extruder, raises the raw materials to a high temperature, the L-ascorbic acid in general is quickly decomposed and inevitably loses its effect as an anti-stress agent.

On the other hand, the L-ascorbic acid derivative used in the anti-stress agent of the present invention maintains its stability even at 100° C. or higher. Accordingly, a heating high-temperature formation can be used for sterilizing or disinfecting the feed or to accelerate conversion of the feed into gluten. Thus, it is not only excellent as an anti-stress agent but also very superior as a feed additive.

EXAMPLES

The present invention is described in greater detail below by reference to the following Examples. However, the present invention should not be construed as being limited thereto.

(Anti-stress agent for animals)

The raw materials in each composition shown below were blended and thoroughly mixed in a mixer to prepare an anti-stress agent for animals. The respective anti-stress agent compositions were designated as Test Segments 1 to 5 and are shown in Table 1.

TABLE 1

| Test Segment No. | Anti-Stress Agent Composition | Blend Composition |
|---|---|---|
| Test Segment 1 | sodium L-ascorbic acid-2-monophosphate | 100% |
| Test Segment 2 | magnesium L-ascorbic acid-2-monophosphate | 100% |
| Test Segment 3 | L-ascorbic acid-2-glucoside | 50% |
|  | magnesium L-ascorbic acid-2-monophosphate | 50% |
| Test Segment 4 | sodium L-ascorbic acid-2-monophosphate | 50% |
|  | dl-α-tocopheryl acetate | 50% |
| Test Segment 5 | calcium L-ascorbic acid-2-monophosphate | 50% |
|  | β-carotene-blended carrot extract | 10% |
|  | mysis extract astaxanthin mixture | 10% |
|  | lutein-blended Marry Gold extract | 10% |
|  | vitamin E-blended wheat germs | 10% |
|  | SOD-blended green alga mixture | 3% |
|  | glutathione-blended yeast | 3% |
|  | catechins-blended green tea extract | 4% |

(Anti-stress feed composition)

To a feed having blended therein 75% (% by weight, hereinafter the same) of corn, 20% of soybean flour (CP: 45%), 1.5% of calcium phosphate and appropriate amounts of an inorganic material mixture, a yeast and an overall vitamin mixture exclusive of ascorbic acids, each of the five kinds of anti-stress agents for animals prepared as described above was blended in a proportion of 600 ppm based on the feed. Each of the blends was thoroughly stirred, subjected to heat (maximum temperature: 100° C.) formation in a normal pellet machine and dried (maximum temperature: 82° C.) to prepare five kinds of anti-stress feed compositions of the present invention.

(Preparation of comparative feed compositions)

Separately, feedstuffs were prepared in the same manner as above, except for using 600 ppm of a blend containing a commercially available heat-resistant grease-coated L-ascorbic acid as shown in Table 2, in place of the anti-stress agent for animals of the present invention.

More specifically, 75% (% by weight, hereinafter the same) of corn, 20% of soybean flour (CP: 45%), 1.5% of calcium phosphate, 0.5% of sodium L-ascorbate and appropriate amounts of an inorganic material mixture, a yeast and an overall vitamin mixture exclusive of ascorbic acids were added and the blend was thoroughly stirred, subjected to heating formation and dried. These compositions were used as the feed for the control segments.

The heating formation and drying of feedstuffs was performed for improving feed efficiency, reducing miscellaneous fungi in the feed and decreasing dust in the livestock house. The conditions thereof were such that the maximum product temperature in the pelletizer was about 70° C. and the drying temperature and time were 50° C. and 20 minutes, respectively. Thereafter, the feedstuffs were stored at room temperature.

TABLE 2

| Control Segment No. | Name of Chemicals | Blend Composition |
|---|---|---|
| Control Segment 1 | grease-coated sodium L-ascorbate | 100% |
| Control Segment 2 | grease-coated magnesium L-ascorbate | 100% |
| Control Segment 3 | grease-coated L-ascorbic acid | 50% |
| | glucose | 25% |
| | magnesium phosphate | 25% |
| Control Segment 4 | grease-coated sodium L-ascorbate | 50% |
| | dl-α-tocopheryl acetate | 50% |
| Control Segment 5 | grease-coated calcium L-ascorbate | 50% |
| | β-carotene-blended carrot extract | 10% |
| | mysis extract astaxanthin mixture | 10% |
| | lutein-blended Marry Gold extract | 10% |
| | vitamin E-blended wheat germs | 10% |
| | SOD-blended green alga mixture | 3% |
| | glutathione-blended yeast | 3% |
| | catechins-blended green tea extract | 4% |

Example 1

(Effect on swine)

In order to verify the effect of the present invention on swine, namely, that the anti-stress agent for animals inhibits the increase of plasma LDH, MDH and AspAT and stress proteins in blood, a test was performed as follows using the feed compositions prepared above as the anti-stress feed composition and the control feed compositions.

100 head of 30 day-old Landrace×Yorkshire boars were divided into 10 groups each consisting of 10 head (20 head equalized in body weight of two groups were taken as one test segment and 5 test segments were formed) and the five kinds of test preparations of the present invention were tested.

For raising the animals, the feed of Test Segment 1 of the present invention was supplied to 10 head of swine in the group of Test Segment 1, and the feed of Control Segment 1 was supplied to 10 head of swine in the group of Control Segment 1. In the same manner, Test Segments 2 to 5 and Control Segments 2 to 5 were formed.

The swine used for this test had been bred with a commercially available vitamin C-free feed until 23-days old exclusive of the lactation and weaning time period.

The highly concentrated L-ascorbic acid-2-phosphate derivative-containing feed prepared above was blended with a general addition-free feed once every morning to achieve oral administration of the L-ascorbic acid-2-phosphate in an amount of about 0.02 mmol per kg body weight and supplied to each test segment. The weight determination was performed once a week, and the amount of the anti-stress agent-containing feed thus added was controlled.

On the other hand, the compositions in the formulation of the control segments was each was blended to have a proportion of 600 ppm and supplied for breeding. In the first day of the test, swine were transferred to a separate swine house to induce stress, and in order to achieve a uniform body weight at the same time period, the group formation was changed. It was confirmed from past experience that this transfer and change of group formation imposes stress on swine and causes problems such as a reduction in incremental body weight. The swine were bred for 60 days from the initiation of the test with the respective feedstuffs of the test segments and the control segments. At the 61st day, blood was sampled from each swine and the blood plasma LDH, MDH and AspAT, the stress proteins in blood and the incremental body weight were determined by the methods described below.

(Determination method of LDH, MDH and AspAT)

The sampled blood was centrifuged at a temperature of 4° C. at 2,000 rpm to separate the plasma, and the supernatant fraction thus obtained was used as a specimen for the determination of enzymes. The enzyme activity was determined by spectroscopically measuring the change in absorbance of NADH at 30° C. and 340 nm. The entire amount of the enzyme reaction solution was 3.0 ml and the test compositions were as follows:

(1) in the case of LDH or MDH:

1.0 ml of 200 mM tris buffer solution (final concentration: 67 mM), 0.1 ml of 5 mM NADH (0.17 mM), 0.1 ml of 30 mM KCl (1 mM), 0.1 ml of 30 mM 2-mercaptoethanol (2-ME), 0.3 ml of substrate (pyruvic acid for LDH, oxaloacetic acid for MDH) (sufficient amount: 5–10 mM), 1.3 ml of water and 0.1 ml of the plasma specimen were added to make a total of 3.0 ml.

(2) in the case of AspAT:

1.0 ml of 200 mM tris buffer solution, 0.1 ml of 5 mM NADH, 0.1 ml of 30 mM KCl, 0.1 ml of 30 mM 2-ME, 0.3 ml of 20 mM α-ketoglutarate, 0.1 ml of an auxiliary enzyme (MDH), 0.3 ml of 50 mM aspartic acid, 0.9 ml of water and 0.1 ml of the plasma specimen were added to make a total of 3.0 ml. The enzyme activity was determined by its initial rate.

(Determination method of stress proteins)

The molecular weight of the stress proteins in plasma, the number of molecular species and the content of each molecular species were determined using a migration diagram obtained by subjecting a gel after SDS-PAGE electrophoresis to protein dyeing. In particular, the content of each protein was obtained as a relative value from its absorbance using a gel scanner. The electrophoresis was performed within the range of not changing the migration conditions of the SDS-PAGE electrophoresis depending on the kind of the plasma specimens from various animals. The results were compared with each other and examined.

(Incremental body weight ratio)

The body weight at the start of the test was measured both in the control segments and the test segments. The incremental body weight after 60 days from the start of the test was obtained according to the following equation, and the values thus obtained were compared.

Incremental body weight=(weight after completing the test in the control segment−weight at the start of the test in the control segment)/(weight after completing the test in the test segment−weight at the start of the test in the test segment)×100

(Results)

The average values of LDH, MDH, AspAT, stress proteins and incremental ratio of the body weight after administering each of the five kinds of anti-stress agents of the present invention as well as the values of the corresponding controls were obtained. Then, the ratio of the present invention to the control was obtained according to the following equation, and the effects were compared.

$$\frac{\text{(average of LDH, MDH, AspAT or stress proteins in the segment where the anti-stress agent of the present invention was administered)}}{\text{(average of LDH, MDH, AspAT or stress proteins in the control segment where an L-ascorbic acid was administered)}} \times 100$$

The results are shown in Table 3. The average values of LDH, MDH, AspAT or stress proteins in blood where the anti-stress agent for animals of the present invention was administered, were markedly reduced as compared with those in the control segments to thereby confirm the effect of the present invention.

Furthermore, an improvement was also obtained with respect to incremental body weight. The effect of administering the anti-stress agent of the present invention containing an antioxidant surpassed the effect that was obtained when an antioxidant was not added.

TABLE 3

|  | Ratio of Test Segment 1 to Control Segment 1 | Ratio of Test Segment 2 to Control Segment 2 | Ratio of Test Segment 3 to Control Segment 3 | Ratio of Test Segment 4 to Control Segment 4 | Ratio of Test Segment 5 to Control Segment 5 |
| --- | --- | --- | --- | --- | --- |
| LDH ratio | 53 | 70 | 63 | 40 | 47 |
| MDH ratio | 74 | 75 | 80 | 55 | 55 |
| AspAT ratio | 64 | 55 | 59 | 58 | 63 |
| Stress protein ratio | 77 | 76 | 80 | 64 | 61 |
| Incremental weight ratio | 30 | 45 | 56 | 18 | 25 |

Example 2
(Effect on cattle)

The following test was performed in order to verify the effect of the present invention on cattle.

50 head in total of 53 day-old Holstein bulls were used, more specifically, 25 head as the segment having the addition of calcium L-ascorbic acid-2-phosphate and 25 head as the segment having no addition. The bulls thus used had been bred with a commercially available vitamin C-free feed until 53-days old exclusive of the lactation and weaning time period.

To a feedstuff containing 30% (% by weight, hereinafter the same) of bran, 20% of barley flour, 44% of rice bran, 5% of soybean cake, 0.5% of salt and appropriate amounts of an inorganic material mixture and an overall vitamin mixture exclusive of ascorbic acids, an anti-stress agent for animals according to the formulation of Test Segment 4 shown in Table 1 was added in a proportion of 600 ppm based on the feedstuff. The blend was thoroughly stirred, subjected to heat formation in a normal pellet machine and dried to prepare an anti-stress feed composition of the present invention.

Separately, a feedstuff having the same composition as above was prepared except for blending a mixture according to the formulation of Control Segment 4 as shown in Table 2 in place of the anti-stress agent for animals of Test Segment 4.

More specifically, 30% (% by weight, hereinafter the same) of bran, 20% of barley flour, 44% of rice bran, 5% of soybean cake, 0.5% of salt, 0.5% of calcium L-ascorbate, 0.25% of inorganic sodium phosphate and appropriate amounts of an inorganic material mixture and an overall vitamin mixture exclusive of ascorbic acids were added, and a mixture according to the formulation of Control Segment 4 shown in Table 2 was added thereto in a proportion of 600 ppm based on the feedstuff. The blend was thoroughly stirred, subjected to heat formation in a normal pellet machine and dried to prepare a control feedstuff.

The heat formation and drying of feedstuffs were performed for improving feeding efficiency and reducing miscellaneous fungi in the feed, and the conditions thereof were such that the maximum product temperature in the pelletizer was about 75° C. and the drying temperature and time were 50° C. and 20 minutes, respectively. Thereafter, the feedstuffs were stored at room temperature.

The bulls in the test segment and the control segment were transported on land over a distance of 567 km by trucks at the initiation of the test and thereafter, the respective feedstuffs were freely supplied over a period of 60 days.

The bulls were raised in this breeding state for 60 days. At the 61st day, blood was sampled from each bull and the blood plasma LDH, MDH and AspAT, the stress proteins in blood and the incremental body weight were determined in the same manner as in Example 1.

From the measurement results, average values were obtained for each segment, and the ratio to the control segment was calculated according to the equation described above. The results are shown in Table 4. The average values of LDH, MDH, AspAT and stress proteins in blood in the segment to which the anti-stress agent for animals of the present invention was administered, were remarkably reduced as compared with those in the control segment to thereby verify the effect of the present invention. Furthermore, an improvement was also obtained with respect to incremental body weight.

TABLE 4

|  | Ratio of Test Segment to Control Segment |
| --- | --- |
| LDH ratio | 53 |
| MDH ratio | 74 |
| ASpAT ratio | 64 |
| Stress protein ratio | 77 |
| Incremental body weight ratio | 30 |

Example 3
(Test of effect on dogs)

12 head in total of pedigree beagles having an average weight of 8.7 kg, more specifically, six head of females and six head of males, were divided into two segments of a test segment and a control segment each having an allocation of three head of females and three head of males. In the test segment, an anti-stress feed composition obtained by adding the components according to the formulation of Test Segment 4 described above to a general beagle feedstuff in a proportion of 600 ppm was supplied and freely fed.

In the control segment, a mixture according to the formulation of Control Segment 4 described above was similarly added to a general beagle feedstuff in a proportion of 600 ppm and freely fed.

The test was performed by breeding the beagles in an open stock-raising house installed in the fields in a high temperature season of summer from August 1 to 30 in 1995. The temperature of the raising house was not particularly controlled.

The beagles were raised in this breeding state for 30 days. On the 31st day, blood was sampled from each beagle and the blood plasma LDH, MDH and AspAT, the stress proteins in blood and the incremental body weight were determined in the same manner as above.

From the measurement results, the average values were obtained for each segment, and the ratio to the control segment was calculated according to the equation described above. The results are shown in Table 5. The average values of LDH, MDH, AspAT and stress proteins in blood in the segment to which the anti-stress agent for animals of the present invention was administered were remarkably reduced despite breeding under high-temperature stress in the summer season as compared with those in the control segment. The effect of the present invention was thus verified. Furthermore, an improvement was also obtained with respect to incremental body weight.

TABLE 5

|  | Ratio of Test Segment to Control Segment |
| --- | --- |
| LDH ratio | 53 |
| MDH ratio | 74 |
| ASpAT ratio | 64 |
| Stress protein ratio | 77 |
| Incremental body weight ratio | 30 |

Example 4

(Effect on marine animals)

60% of fish meal, 10% of cuttlefish meal, 12.5% of gluten, 1.5% of cod liver oil, 0.1% of β-carotene, 1% of sodium dihydrogenphosphate, 1.5% of sodium hydrogenphosphate, 1.4% of vitamin premix exclusive of vitamin C, 0.02% of ethoxychin, 600 ppm of the anti-stress agent for animals of Test Segment 4 described above and a corn gluten as a balance were added to make 100%. These raw materials were crushed, thoroughly mixed in a mixer and formed in a pellet mill into a feedstuff for marine animals such as rainbow trout, sweet fish, carp, sea bream, salmon, eel, yellow tail, globefish, flatfish, tuna, horse mackerel and prawn.

Comparative Example 2

A feedstuff having the same composition was prepared by the same production method as in Example 4 except for using 600 ppm of a mixture according to the formulation of Control Segment 4 described above. The feedstuff obtained was administered in raising rainbow trout, sweet fish, carp, sea bream, salmon, eel, yellow tail, globefish, flatfish, tuna or horse mackerel, and the culturing test was performed for a period of over 100 days. At the 101st day, 20 fish from the respective marine animals were randomly selected and the blood was sampled therefrom. The blood plasma LDH and AspAT were determined in the same manner as described above, and the ratio of the Test Segment to the Control Segment was obtained in the same manner as described above. Furthermore, the survival rate of the respective marine animals was determined at the end of test, and the effectiveness on marine animals was examined. The results are shown in Table 6.

TABLE 6

| Production species | rainbow trout | sweet-fish | carp | sea bream | salmon | eel | yellow-tail | globe-fish | flat-fish | tuna | horse mackerel |
| --- | --- | --- | --- | --- | --- | --- | --- | --- | --- | --- | --- |
| LDH ratio | 65% | 59% | 84% | 89% | 76% | 85% | 45% | 64% | 75% | 55% | 68% |
| AspAT ratio | 65% | 59% | 84% | 89% | 76% | 85% | 45% | 64% | 75% | 55% | 68% |
| Survival rate[1] in test segment at the end of culturing test | 95% | 85% | 99% | 88% | 90% | 90% | 89% | 87% | 98% | 95% | 89% |
| Survival rate[1] in control segment at the end of culturing test | 75% | 65% | 90% | 75% | 83% | 82% | 69% | 80% | 88% | 84% | 80% |

[1] survival rate = $\dfrac{\text{number of surviving animals the end of test}}{\text{number of animals at the initiation of the test}} \times 100\ (\%)$ When an animal is placed under stress, a stress reaction such as an increase or fluctuation of LDH, MDH and AspAT in blood is observed. This is a very important physiological index for showing stress, and in order to overcome the stress, an L-ascorbic acid has hitherto been added to feed for animals. However, the L-ascorbic acid derivative in general has poor heat resistance and cannot exert a sufficiently high effect as a feed additive. L-ascorbic acid derivatives having good heat resistance have also been developed, however, these derivatives can hardly be converted into L-ascorbic acid by internal enzymes in some living animals and the L-ascorbic acid activity cannot be satisfactorily provided.

On the other hand, L-ascorbic acid-2-phosphoric acid, a salt thereof, an L-ascorbic acid-2-glucoside and a salt thereof used as anti-stress agents of the present invention are not only highly heat resistant but also capable of decomposition by an internal enzyme to convert the same into L-ascorbic acid, to thereby provide high L-ascorbic acid activity. Thus, they are not only useful as anti-stress agents but also are very excellent as a feed additive. By using the anti-stress agents of the present invention, the stress reaction of animals can be prevented, and various disorders accompanying stress in the breeding of useful animals, such as a loss in weight or a reduction in immunity, can be inhibited.

While the invention has been described in detail and with reference to specific embodiments thereof, it will be apparent to one skilled in the art that various changes and modifications can be made therein without departing from the spirit and scope thereof.

What is claimed is:

1. A method for inhibiting in animals an increase of blood plasma lactate dehydrogenase (LDH), malate dehydrogenase (MDH) and aspartate aminotransferase (AspAT) and for inhibiting an increase of stress proteins in blood, occurring when said animals are subjected to stress, which comprises administering to animals an anti-stress agent comprising one or more substances selected from the group consisting of L-ascorbic acid-2-monophosphoric acid and a salt thereof as an active ingredient.

2. The method as claimed in claim 1, wherein said anti-stress agent further comprises an antioxidant blended with the one or more substances selected from the group consisting of L-ascorbic acid-2-monophosphoric acid and a salt thereof.

3. The method as claimed in claim 2, wherein the antioxidant is selected from the group consisting of carotene, astaxanthin, lutein, dl-α-tocopheryl acetate, α-tocopherol, SOD, glutathione and catechins.

4. A method for inhibiting in animals an increase of blood plasma lactate dehydrogenase (LDH), malate dehydrogenase (MDH) and aspartate aminotransferase (AspAT) and for inhibiting an increase of stress proteins in blood, occurring when said animals are subjected to stress, which comprises administering to animals, as a premix, an animal drug or a nutrient reinforcement, a feed composition having blended therewith an anti-stress agent comprising one or more substances selected from the group consisting of L-ascorbic acid-2-monophosphoric acid and a salt thereof as an active ingredient.

5. The method as claimed in claim 4, wherein said anti-stress agent further comprises an antioxidant blended with the one or more substances selected from the group consisting of L-ascorbic acid-2-monophosphoric acid and a salt thereof.

6. The method as claimed in claim 5, wherein the antioxidant is selected from the group consisting of carotene, astaxanthin, lutein, dl-α-tocopheryl acetate, α-tocopherol, SOD, glutathione and catechins.

7. A method of reducing stress in animals, which comprises administering 0.03 g/kg-body weight or more of one or more substances selected from the group consisting of L-ascorbic acid-2-monophosphoric acid and a salt thereof for inhibiting an increase of blood plasma lactate dehydrogenase (LDH), malate dehydrogenase (MDH) and aspartate aminotransferase (AspAT) and for inhibiting an increase of stress proteins in blood, which occur when said animals are subjected to stress.

8. The method of reducing stress in animals as claimed in claim 7, wherein said animal is selected from the group consisting of cattle, pigs, dogs, cats, rainbow trout, sweet fish, carp, sea bream, salmon, eel, yellow tail, globefish, flatfish, tuna, horse mackerel and prawn.

9. A method of reducing stress in animals, which comprises simultaneously administering 0.03 g/kg-body weight or more of one or more substances selected from the group consisting of L-ascorbic acid-2-monophosphoric acid and a salt thereof as an active ingredient, and 0.02 g/kg-body weight or more of another antioxidant, for inhibiting an increase of blood plasma lactate dehydrogenase (LDH), malate dehydrogenase (MDH) and aspartate aminotransferase (AspAT) and for inhibiting an increase of stress proteins in blood, which occur when said animals are subjected to stress.

10. The method of reducing stress in animals as claimed in claim 9, wherein said animal is selected from the group consisting of cattle, pigs, dogs, cats, rainbow trout, sweet fish, carp, sea bream, salmon, eel, yellow tail, globefish, flatfish, tuna, horse mackerel and prawn.

11. A feed composition prepared by blending with animal feed an anti-stress agent for animals containing one or more substances selected from the group consisting of L-ascorbic acid-2-monophosphoric acid and a salt thereof as an active ingredient, in a blending ratio of 300 ppm or more in terms of the active ingredient.

12. The feed composition as claimed in claim 11, wherein the feed composition prepared by blending with animal feed an anti-stress agent for animals containing 300 ppm or more of one or more substances selected from the group consisting of L-ascorbic acid-2-monophosphoric acid and a salt thereof as an active ingredient, is a feed composition heated at 80° C. or higher in an extruder, expander, pellet machine or dryer.

13. A feed composition prepared by blending with animal feed an anti-stress agent for animals containing 300 ppm or more of one or more substances selected from the group consisting of L-ascorbic acid-2-monophosphoric acid and a salt thereof as an active ingredient and 200 ppm or more of an antioxidant substance.

14. The feed composition as claimed in claim 13, wherein the feed composition prepared by blending with animal feed an anti-stress agent for animals containing 300 ppm or more of one or more substances selected from the group consisting of L-ascorbic acid-2-monophosphoric acid and a salt thereof as an active ingredient, and 200 ppm or more of an antioxidant substance, is a feed composition heated at 80° C. or higher in an extruder, expander, pellet machine or dryer.

15. A method of reducing stress in animals, which comprises supplying a feed composition prepared by blending with animal feed an anti-stress agent for animals containing 300 ppm or more of one or more substances selected from the group consisting of L-ascorbic acid-2-monophosphoric acid and a salt thereof as an active ingredient, to cattle, pigs, dogs, cats, rainbow trout, sweet fish, carp, sea bream, salmon, eel, yellow tail, globefish, flatfish, tuna, horse mackerel or prawn.

16. The method as claimed in claim 15, which further comprises blending with the animal feed 200 ppm or more of an antioxidant substance.

\* \* \* \* \*